United States Patent
Tazawa

(10) Patent No.: US 12,150,892 B2
(45) Date of Patent: Nov. 26, 2024

(54) OPHTHALMIC TWEEZERS

(71) Applicant: MANI, INC., Tochigi (JP)

(72) Inventor: Yoshiyuki Tazawa, Tochigi (JP)

(73) Assignee: MANI, INC., Tochigi (JP)

( * ) Notice: Subject to any disclaimer, the term of this patent is extended or adjusted under 35 U.S.C. 154(b) by 414 days.

(21) Appl. No.: 17/286,305

(22) PCT Filed: Feb. 25, 2020

(86) PCT No.: PCT/JP2020/007549
§ 371 (c)(1),
(2) Date: Apr. 16, 2021

(87) PCT Pub. No.: WO2020/179550
PCT Pub. Date: Sep. 10, 2020

(65) Prior Publication Data
US 2022/0096268 A1    Mar. 31, 2022

(30) Foreign Application Priority Data
Mar. 6, 2019    (JP) .................................. 2019-040976

(51) Int. Cl.
*A61F 9/007*    (2006.01)
*A61B 17/30*    (2006.01)

(52) U.S. Cl.
CPC .......... *A61F 9/00736* (2013.01); *A61B 17/30* (2013.01)

(58) Field of Classification Search
CPC ........................... A61F 9/00736; A61B 17/30; A61B 2017/305
(Continued)

(56) References Cited

U.S. PATENT DOCUMENTS 5,222,973 A * 6/1993 Sharpe .................. A61B 17/29
                                                    294/99.2
5,527,313 A    6/1996 Scott et al.
(Continued)

FOREIGN PATENT DOCUMENTS

CN        205849641 U    1/2017
CN        108095805 A    6/2018
(Continued)

OTHER PUBLICATIONS

Office Action issued on Apr. 8, 2021 for Australian Patent Application No. 2020233742.
(Continued)

*Primary Examiner* — Kankindi Rwego
(74) *Attorney, Agent, or Firm* — Pearne & Gordon LLP

(57) ABSTRACT

There are provided ophthalmic tweezers capable of easily adjusting the strength of a gripping force depending on use conditions. Ophthalmic tweezers (10) include a tweezers section (20) which has a tubular body (21), a pair of neck portions (22), and a pair of grippers (23) located on the leading end side of the neck portions (22). The tweezers section (20) has a structure in which the grippers (23) are closed by causing the tubular body (21) to slide such that the neck portions (22) are housed in the inner cavity of the tubular body (21). The neck portions (22) each have a first curved or bent portion (22a) having a convex shape on the central axis side of the tubular body (21) and a second curved or bent portion (22b) having a concave shape on the central axis side of the tubular body (21). The first curved or bent portion (22a) is located on the tubular body side, and the second curved or bent portion (22b) is located on the gripper side.

4 Claims, 3 Drawing Sheets

(58) Field of Classification Search
USPC .................................................... 606/107
See application file for complete search history.

(56) References Cited

U.S. PATENT DOCUMENTS

| | | |
|---|---|---|
| 9,827,141 B2 | 11/2017 | Schaller et al. |
| 10,092,168 B1 | 10/2018 | Huttner et al. |
| 10,406,027 B2 | 9/2019 | Grueebler et al. |
| 2008/0188877 A1 | 8/2008 | Hickingbotham |
| 2011/0015669 A1 | 1/2011 | Corcosteugi |
| 2011/0295289 A1 | 12/2011 | Andre |
| 2014/0135820 A1 | 5/2014 | Schaller et al. |
| 2014/0172010 A1 | 6/2014 | Vezzu |
| 2014/0379024 A1 | 12/2014 | Schaller et al. |
| 2015/0238355 A1 | 8/2015 | Vezzu et al. |
| 2015/0359669 A1 | 12/2015 | Grueebler et al. |
| 2017/0086871 A1 | 3/2017 | Scheller et al. |
| 2017/0348013 A1 | 12/2017 | Mottola et al. |
| 2018/0368911 A1 | 12/2018 | van Overdam |
| 2019/0000670 A1 | 1/2019 | Grueebler |
| 2019/0357928 A1 | 11/2019 | Hassan et al. |

FOREIGN PATENT DOCUMENTS

| | | | |
|---|---|---|---|
| CN | 109820640 | A | 5/2019 |
| CN | 209377865 | U | 9/2019 |
| DE | 10-2009-033015 | A1 | 1/2011 |
| JP | 2017-506111 | A | 3/2017 |
| JP | 2017-517326 | A | 6/2017 |
| RU | 15644 | U1 | 11/2000 |
| RU | 2319475 | C2 | 3/2008 |
| RU | 2011-135848 | U1 | 3/2013 |
| RU | 185416 | U1 | 12/2018 |
| TW | 2014-34431 | A | 9/2014 |
| TW | 2015-21665 | A | 6/2015 |
| WO | 2010/126076 | A1 | 11/2010 |
| WO | 2013-120491 | A1 | 8/2013 |
| WO | 2020-179550 | A1 | 9/2020 |

OTHER PUBLICATIONS

European Search Report issued on Mar. 15, 2021 for European Patent Application No. 20197410.2.
Pamphlet "The Benchmark for Vitreoretinal Single-Use Instruments".
Notice of Opposition dated Jan. 5, 2023 for European Patent Application No. 20197410.2.
United States Office Action dated Jun. 7, 2022 issued in U.S. Appl. No. 17/022,854.
United States Office Action dated Oct. 11, 2022 issued in U.S. Appl. No. 17/022,854.
International Search Report dated May 26, 2020 filed in PCT/JP2020/007549.
Office Action issued on Jul. 28, 2022 for the corresponding JP Patent Application No. JP2021-503987.

* cited by examiner (a)

(b)

OPHTHALMIC TWEEZERS

TECHNICAL FIELD

The present invention relates to ophthalmic tweezers used in ophthalmic surgery.

BACKGROUND ART

In ophthalmic surgery such as vitreous surgery, cataract surgery, and glaucoma surgery, gripping and treating an eye tissue or the like are performed. In such ophthalmic surgery, an ophthalmic surgical instrument or the like are used inside an eyeball by firstly attaching a cannula to an eyeball and inserting an ophthalmic surgical instrument or the like through the cannula (see, for example, PATENT LITERATURE 1). An example of such an ophthalmic surgical instrument is ophthalmic tweezers to grasp and treat an eye tissue such as a vitreous body.

FIG. 4 is an in-use view of known ophthalmic tweezers. Here, a commonly used cannula 40 mounted on an eyeball E in vitreous surgery has a structure in which the vicinity of the base end of a metal pipe is inset into a resin base.

The leading end side of ophthalmic tweezers 100 constitutes a tweezers section 20 to grasp a vitreous body, and the tweezers section 20 is inserted inside the eyeball E through the cannula 40. The structure of the tweezers section 20 includes grippers 23 at the leading end and neck portions 22 disposed continuously from the grippers 23. Furthermore, a portion on the base end side from the neck portions 22 is housed in the inner cavity of a tubular body 21. Since the tubular body 21 is inserted inside the eyeball E, an extraordinarily thin material is used as the tubular body 21. Furthermore, for preventing the tubular body 21 from bending outside the cannula 40 during work, the outside of the tubular body 21 is reinforced with a reinforcing sleeve 33 in some cases.

The basic structure of the ophthalmic tweezers 100 has a body portion 35 outside the tubular body 21 through another component and a sliding member 37 at a position to slide relative to the body portion 35. Here, the sliding member 37 and the tubular body 21 are connected to each other. When operators 36 are closed or opened, the sliding member 37 connected from the operators 36 via a biasing device such as a leaf spring moves in the axial direction relative to the body portion 35, and the tubular body 21 connected to the sliding member 37 slides in the axial direction. Accordingly, the neck portions 22 enter or exit from the inner cavity of the tubular body 21, so that the grippers 23 are closed when the neck portions 22 enter the inner cavity of the tubular body 21, and the grippers open when the neck portions 22 exit outside the tubular body 21. In brief, the grippers 23 of the tweezers section 20 are closed when the operators 36 are closed with fingers, and the grippers 23 open when the operators 36 open by releasing the fingers. It is noted that although the ophthalmic tweezers 100 include the reinforcing sleeve 33, the reinforcing sleeve 33 may not be disposed. Also, the sliding member 37 may be disposed either inside or outside the body portion 35.

However, such known ophthalmic tweezers basically merely either close or open the grippers, and adjustment of the gripping force is an extraordinarily difficult work.

CITATION LIST

Patent Literature

PATENT LITERATURE 1: WO 2010/126076 A

SUMMARY OF INVENTION

Problems to be Solved by Invention

In view of such circumstances, the present invention has as its object to provide ophthalmic tweezers capable of easily adjusting the strength of a gripping force depending on use conditions.

Solution to Problems

Ophthalmic tweezers according to the present invention includes a tweezers section, the tweezers section including: a tubular body; a pair of neck portions; and a pair of grippers located on the leading end side of the neck portions. The tweezers section has a structure in which the grippers are closed by causing the tubular body to slide such that the neck portions are housed in an inner cavity of the tubular body, and the neck portions each have a first curved or bent portion having a convex shape on the central axis side of the tubular body and a second curved or bent portion having a concave shape on the central axis side of the tubular body, and the first curved or bent portion is located on the tubular body side, and the second curved or bent portion is located on the gripper side.

Also, it may be configured that the grippers contact each other when the first curved or bent portions are housed in the inner cavity of the tubular body, and the gripping force of the grippers is improved when the second curved or bent portions are housed in the inner cavity of the tubular body.

Effects of Invention

According to the present invention, a gripping force clearly differs between when only the first curved or bent portions are housed in the inner cavity of the tubular body and when the second curved or bent portions are additionally housed in the inner cavity of the tubular body. This exerts the effect that adjustment of a gripping force is facilitated.

Also, when it is configured that the grippers contact each other when the first curved or bent portions are housed in the inner cavity of the tubular body, and the gripping force of the grippers is improved when the second curved or bent portions are housed in the inner cavity of the tubular body, only the first curved or bent portions are housed in the inner cavity of the tubular body when it is desired to lightly pick up an object, and the second curved or bent portions are additionally housed when it is desired to tightly pinch the object. This facilitates different uses depending on use conditions.

BRIEF DESCRIPTION OF DRAWINGS

FIG. 2(a) is a view in which a tweezers section is open; FIG. 2(b) is a view in which a tweezers section is lightly closed; and FIG. 2(c) is a view in which the gripping force of a pair of grippers is strengthened.

DESCRIPTION OF EMBODIMENTS

Hereinafter, embodiments of the present invention will be described with reference to the attached drawings.

Figure 1:
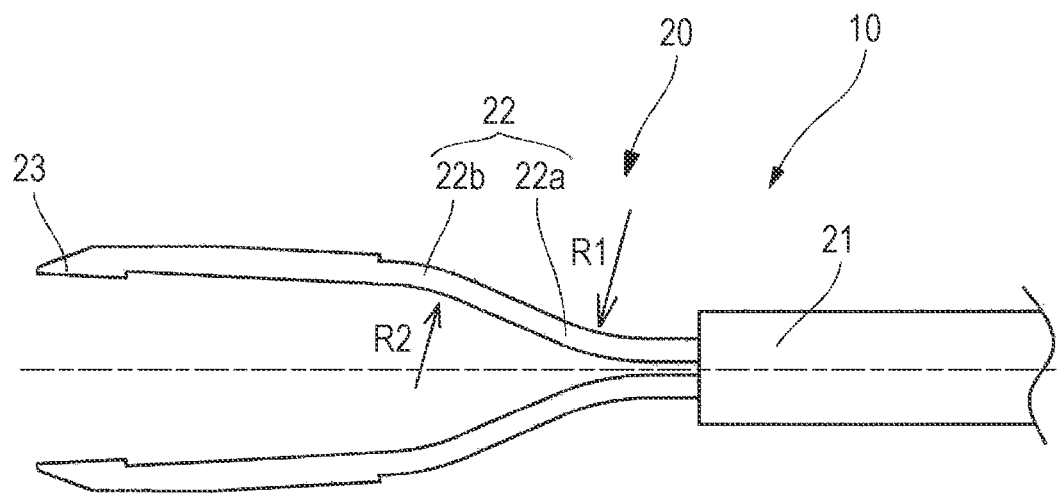
FIG. 1 is an enlarged view of a tweezers section according to ophthalmic tweezers of the present invention.

FIG. 1 is an enlarged view of a tweezers section according to ophthalmic tweezers of the present invention.

The basic action of ophthalmic tweezers 10 is that, similarly to the previously-described known ophthalmic tweezers, the grippers 23 of the tweezers section 20 are closed when the operators are closed with fingers, and the grippers 23 open when the operators are opened.

The structure of the tweezers section 20 of the ophthalmic tweezers 10 includes a tubular body 21, a pair of neck portions 22, and a pair of grippers 23 located on the leading end side of the neck portions 22. Although not illustrated, the base end side from the neck portions 22 is fixed to around the base of the operators through the inside of the tubular body 21.

When the operators are closed with fingers, the tubular body 21 slides in the axial direction so that the neck portions 22 are housed in the inner cavity of the tubular body 21, and the grippers 23 at the leading end are closed.

Here, it is configured that the neck portions 22 each have a first curved or bent portion 22a on the tubular body side and a second curved or bent portion 22b on the gripper side. The first curved or bent portion 22a has a convex curve shape on the central axis side of the tubular body 21, and the second curved or bent portion 22b has a concave curve shape on the centred axis side of the tubular body 21. In other words, the central axis of the tubular body 21 is located on the outer side of the first curved or bent portion 22a and on the inner side of the second curved or bent portion 22b.

Figure 2:
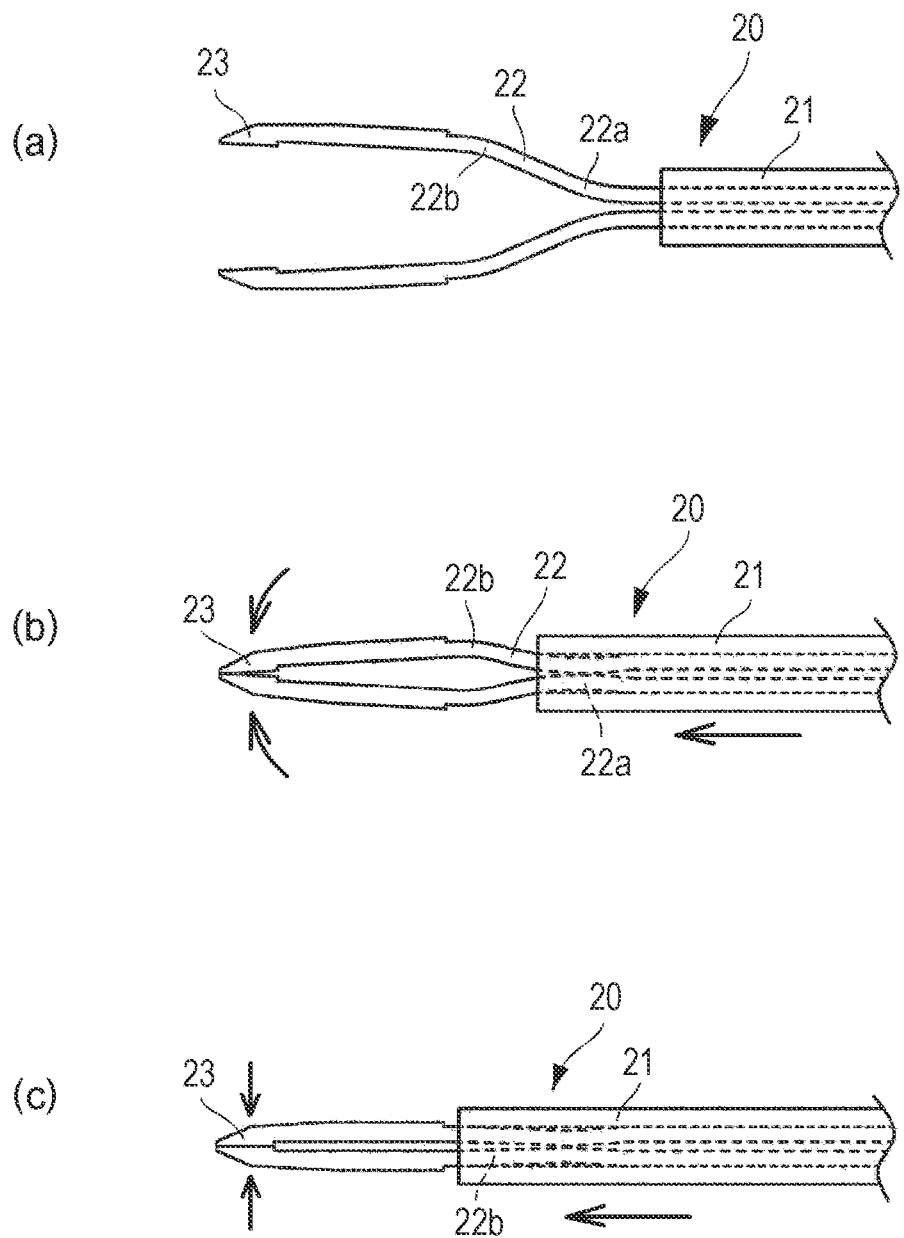
FIGS. 2(a) to 2(c) are views illustrating movement of a tweezers section.

Here, the movement of the tweezers section 20, when the tubular body 21 is caused to slide such that the neck portions 22 are housed in the inner cavity of the tubular body 21 thereby to close the grippers 23, will be described using the drawings. FIGS. 2(a) to 2(c) are views illustrating movement of a tweezers section 20; FIG. 2(a) is a view in which a tweezers section 20 is open; FIG. 2(b) is a view in which a tweezers section 20 is lightly closed; and FIG. 2(c) is a view in which the gripping force of a pair of grippers 23 is strengthened.

When the neck portions 22 are not housed in the inner cavity of the tubular body 21 as illustrated in FIG. 2(a), the grippers 23 are apart from each other, and the tweezers section 20 is open. Then, when the tubular body 21 is caused to slide such that the first curved or bent portions 22a of the neck portions 22 are housed in the inner cavity of the tubular body 21, the grippers 23 contact each other from the leading end side so that the tweezers section 20 are lightly closed as illustrated in FIG. 2(b). In this state, the maximum width when the second curved or bent portions 22b facing each other are connected is larger than the inner diameter of the tubular body 21.

Furthermore, when the tubular body 21 is caused to slide such that the second curved or bent portions 22b are additionally housed in the inner cavity of the tubular body 21, the second curved or bent portions 22b serve as a spring so that the grippers 23 are closed more tightly. Here, since the second curved or bent portions 22b each have a concave curve shape on the central axis side of the tubular body 21, the gripping force of the grippers 23 is strengthened when the tubular body 21 is caused to slide, until the tops of the curves are housed in the inner cavity of the tubular body 21. In brief, not only the grippers are either closed or open like the known ophthalmic tweezers, but also the gripping force can be adjusted.

It is noted that the curve direction of the first curved or bent portion 22a and the curve direction of the second curved or bent portion 22b are opposite each other, and the resistance force when the operators are closed differs between before and after the grippers 23 contact each other. Accordingly, the state of the gripping force is reflected on the operators of fingers. This relatively facilitates the adjustment of the gripping force.

Here, the curvature radius R1 of the first curved or bent portions 22a has to be determined in consideration of the fact that the leading ends of the grippers 23 contact each other when the first curved or bent portions 22a are housed in the inner cavity of the tubular body 21. Also, the curvature radius R2 of the second curved or bent portions 22b has to be determined in consideration of a force as spring when the second curved or bent portions 22b are housed into the inner cavity of the tubular body 21.

Figure 3:
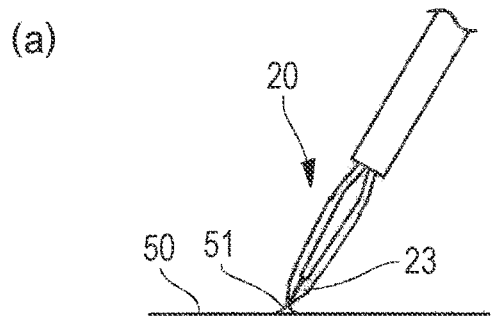
FIGS. 3(a) and 3(b) are views illustrating a use method of ophthalmic tweezers.
Figure 3:
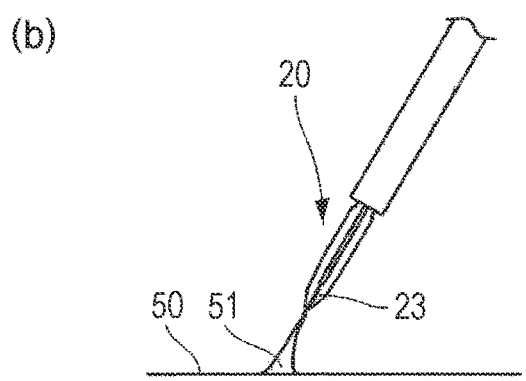
Figure 4:
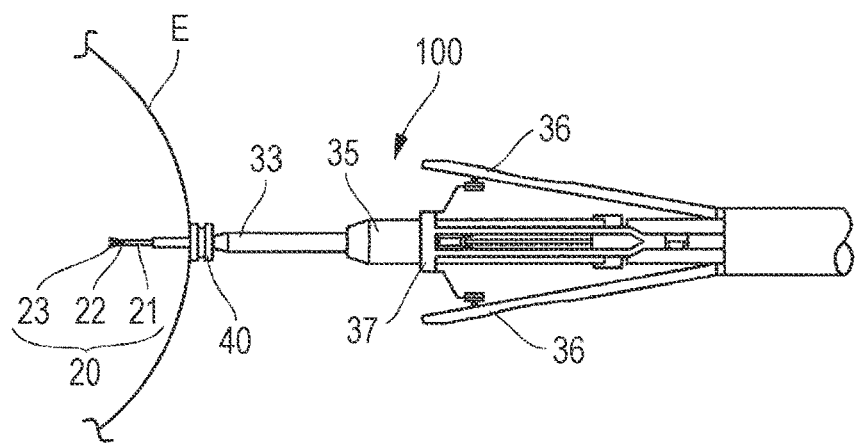
FIG. 4 is an in-use view of known ophthalmic tweezers.

Next, actual use situations in which the grippers 23 are lightly or tightly closed will be described. FIGS. 3(a) and 3(b) are views illustrating a use method of the ophthalmic tweezers.

FIG. 3(a) is a view in which a proliferative membrane 51 on a retina 50 is pulled. When the proliferative membrane 51 almost contacts the retina 50 in this manner, the proliferative membrane 51 needs to be lightly picked up and pulled up by the grippers 23. It is noted that when the gripping force is excessively strong in this case, the proliferative membrane 51 can be broken. Therefore, the gripping force should not be excessively strong, and it is enough to lightly pick up the proliferative membrane 51.

After the proliferative membrane 51 has been pulled up to some extent, the proliferative membrane 51 needs to be tightly pinched as illustrated in FIG. 3(b) for removal. At this time, the gripping force is required to be strengthened such that the proliferative membrane 51 does not drop. It is noted that, other than the above-described use method, there is a case in which the adjustment of the gripping force is necessary, and the present invention has the merit that such adjustment of the gripping force can be achieved. Also, although an example in which an eye tissue is grasped has been described herein, the ophthalmic tweezers according to the present invention can also be used for, for example, grasping an ophthalmic instrument such as an intraocular lens.

Also, in other words, the use method of picking up air object by the eating ends of the grippers 23 is performed when only the first curved or bent portions 22a are housed in the inner cavity of the tubular body 21, and the use method of pinching an object by the entireties of the grippers is performed when the second curved or bent portions 22b are additionally housed in the inner cavity of the tubular body 21. In brief, according to the ophthalmic tweezers of the present invention, one type of ophthalmic tweezers can achieve the characteristics of two types of ophthalmic tweezers: one with grippers having a shape for picking up and the other with grippers having a shape for pinching.

LIST OF REFERENCE SIGNS 10 ophthalmic tweezers
20 tweezers section
21 tubular body
21a central axis of tubular body
22 neck portion
22a first curved or bent portion
22b second curved or bent portion
23 gripper
33 reinforcing sleeve
35 body portion
36 operator
37 sliding member 40 cannula
50 retina
51 proliferative membrane

The invention claimed is:

1. Ophthalmic tweezers comprising a tweezers section, the tweezers section including:
   a tubular body;
   a pair of neck portions; and
   a pair of grippers located on a leading end side of the pair of neck portions, wherein
   the tweezers section has a structure in which the pair of grippers are closed by causing the tubular body to slide such that the pair of neck portions are housed in an inner cavity of the tubular body,
   the pair of neck portions each have a first curved or bent portion having a convex shape on a central axis side of the tubular body and a second curved or bent portion having a concave shape on the central axis side of the tubular body, and the first curved or bent portion is located on the tubular body side, and the second curved or bent portion is located on the gripper side,
   leading ends of the pair of grippers contact each other when the first curved or bent portions are housed in the inner cavity of the tubular body, and
   an entirety of the pair of grippers contacts each other when the second curved or bent portions are housed in the inner cavity of the tubular body.

2. The ophthalmic tweezers according to claim 1, wherein a gripping force of the pair of grippers is improved when the second curved or bent portions are housed in the inner cavity of the tubular body.

3. The ophthalmic tweezers according to claim 1, wherein the pair of grippers each have based ends opposing the leading ends,
   when the leading ends of the pair of grippers contact each other and the base ends of the pair of grippers are not in contact with each other, the first curved or bent portions are fully housed in the inner cavity of the tubular body and the second curved or bent portions are located outside the inner cavity of the tubular body.

4. The ophthalmic tweezers according to claim 1, wherein when the first curved or bent portions are fully housed in the inner cavity of the tubular body and the second curved or bent portions are located outside the inner cavity of the tubular body, a maximum width between the second curved or bent portions are larger than an inner diameter of the inner cavity of the tubular body.

* * * * *

UNITED STATES PATENT AND TRADEMARK OFFICE
CERTIFICATE OF CORRECTION

| | |
|---|---|
| PATENT NO. | : 12,150,892 B2 |
| APPLICATION NO. | : 17/286305 |
| DATED | : November 26, 2024 |
| INVENTOR(S) | : Yoshiyuki Tazawa |

It is certified that error appears in the above-identified patent and that said Letters Patent is hereby corrected as shown below:

In the Specification

Column 3, Line 25, delete "on the centred axis side" and insert --on the central axis side--.

Signed and Sealed this
Tenth Day of June, 2025

Coke Morgan Stewart
*Acting Director of the United States Patent and Trademark Office*